(12) United States Patent
Konno et al.

(10) Patent No.: US 10,485,424 B2
(45) Date of Patent: Nov. 26, 2019

(54) RELAY DEVICE

(71) Applicant: NIHON KOHDEN CORPORATION, Shinjuku-ku, Tokyo (JP)

(72) Inventors: Norihito Konno, Tokyo (JP); Hirohiko Ikeya, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 16/099,054

(22) PCT Filed: Jun. 13, 2017

(86) PCT No.: PCT/JP2017/021763
§ 371 (c)(1),
(2) Date: Nov. 5, 2018

(87) PCT Pub. No.: WO2018/003486
PCT Pub. Date: Jan. 4, 2018

(65) Prior Publication Data
US 2019/0133443 A1 May 9, 2019

(30) Foreign Application Priority Data

Jun. 28, 2016 (JP) ................. 2016-127895

(51) Int. Cl.
*A61B 5/00* (2006.01)
*G16H 40/67* (2018.01)
*G08B 21/18* (2006.01)

(52) U.S. Cl.
CPC .............. *A61B 5/002* (2013.01); *A61B 5/746* (2013.01); *G08B 21/182* (2013.01); *G16H 40/67* (2018.01); *A61B 2560/0214* (2013.01); *A61B 2562/08* (2013.01); *A61B 2562/222* (2013.01)

(58) Field of Classification Search
CPC .................................. H05L 1/00; G05B 1/00
See application file for complete search history.

(56) References Cited

U.S. PATENT DOCUMENTS

| 8,558,933 | B2 | 10/2013 | Sakai | |
| 2006/0066449 | A1* | 3/2006 | Johnson | ................ A61B 5/1113 340/539.12 |
| 2010/0280339 | A1 | 11/2010 | Russ | |
| 2011/0202371 | A1* | 8/2011 | Darguesse | ............. G06Q 50/24 705/3 |

(Continued)

OTHER PUBLICATIONS

International Search Report issued in Patent Application No. PCT/JP2017/021763 dated Mar. 2, 2018.

(Continued)

*Primary Examiner* — Shirley Lu
(74) *Attorney, Agent, or Firm* — Pearne & Gordon LLP

(57) ABSTRACT

A relay device (1) including: an authentication unit (11) which authenticates a sensor present within a predetermined range; an acquisition unit (12) which can acquire, from the sensor authenticated by the authentication unit (11), vital information of a patient measured by the sensor; a storage unit (13) in which a bed ID associated with a bed is stored; and a transmission unit (14) which associates the bed ID with the vital information acquired by the acquisition unit (12) and then transmits the vital information including the bed ID to a bedside monitor.

8 Claims, 3 Drawing Sheets

(56) References Cited

U.S. PATENT DOCUMENTS

| | | | |
|---|---|---|---|
| 2012/0003933 A1* | 1/2012 | Baker | H04W 76/38 455/41.2 |
| 2015/0302150 A1 | 10/2015 | Mazar et al. | |
| 2016/0157719 A1* | 6/2016 | Spector | A61B 5/742 340/870.07 |

OTHER PUBLICATIONS

Written Opinion issued in Patent Application No. PCT/JP2017/021763 dated Mar. 2, 2018.

* cited by examiner

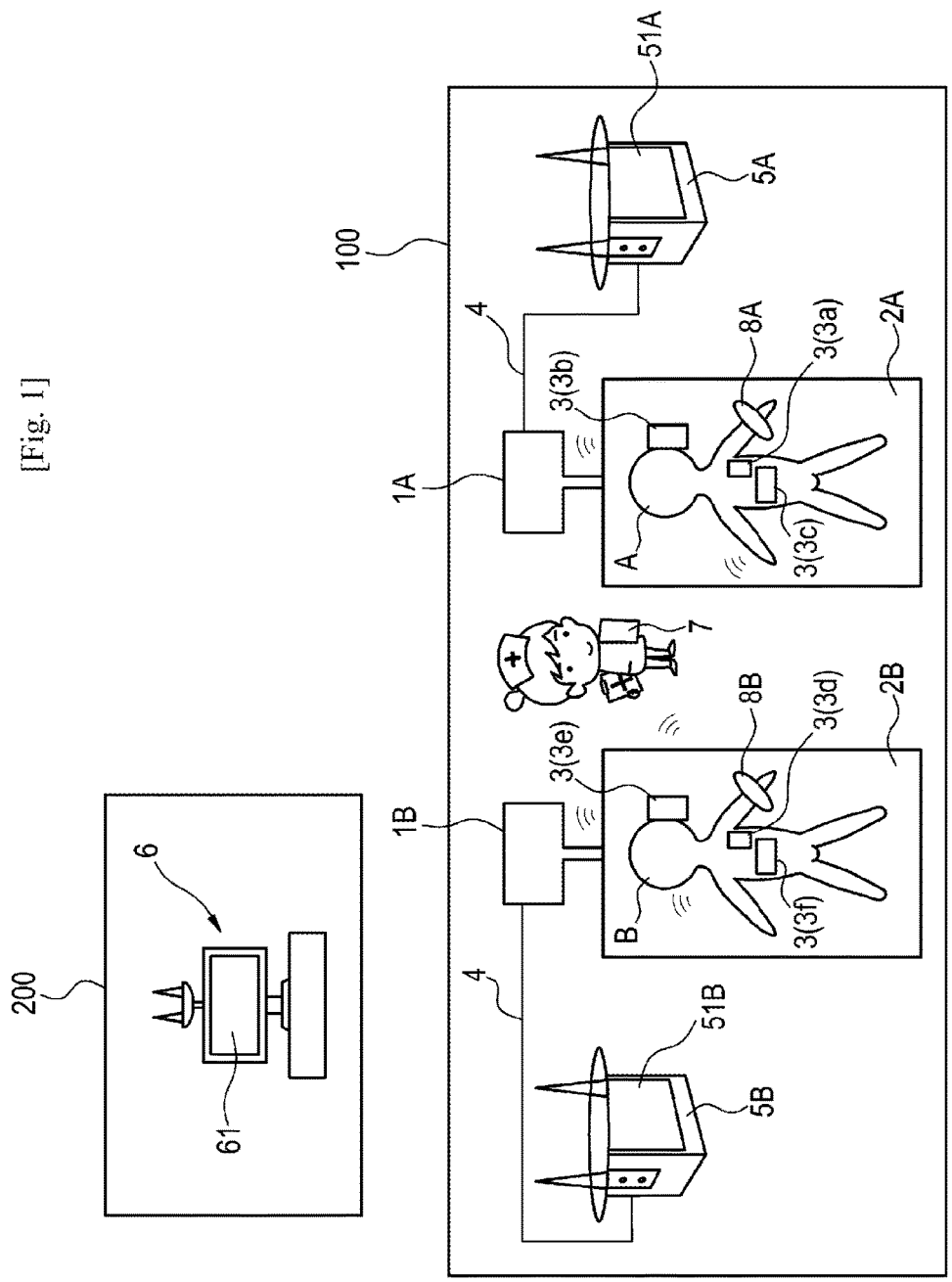

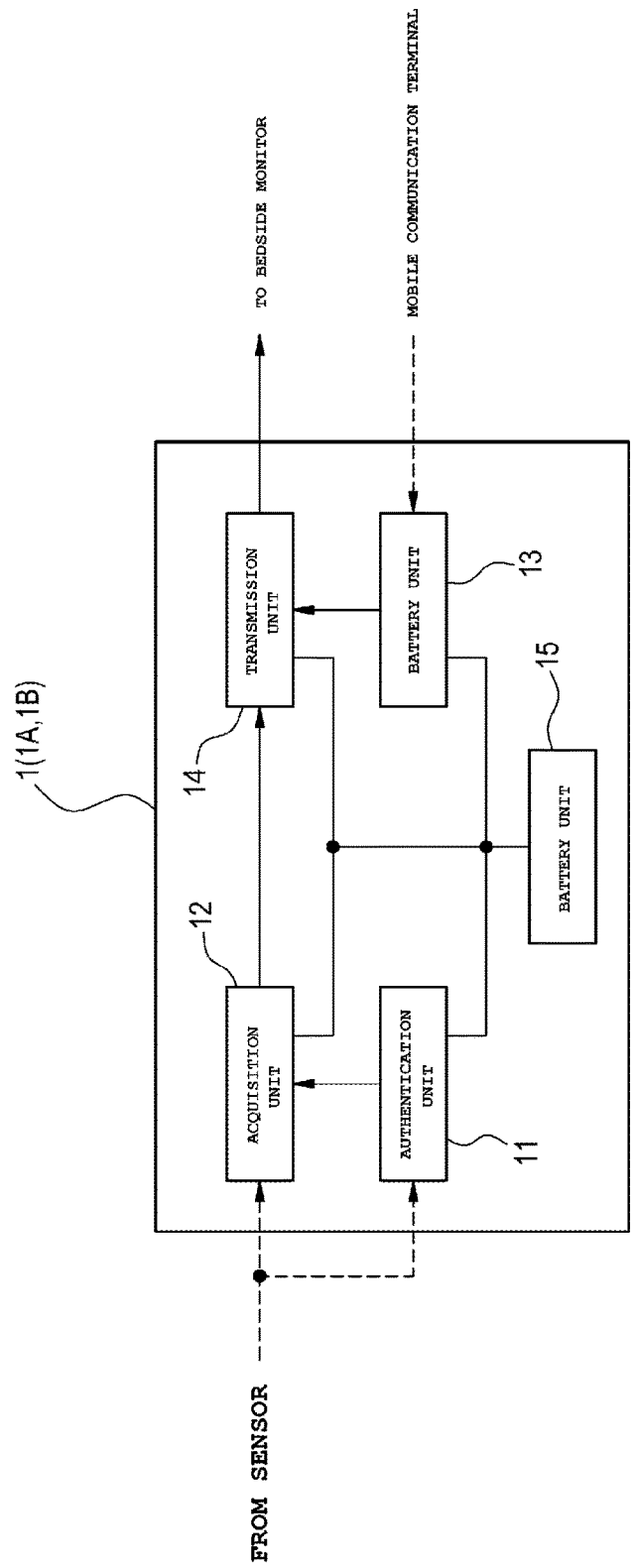

[Fig. 3]
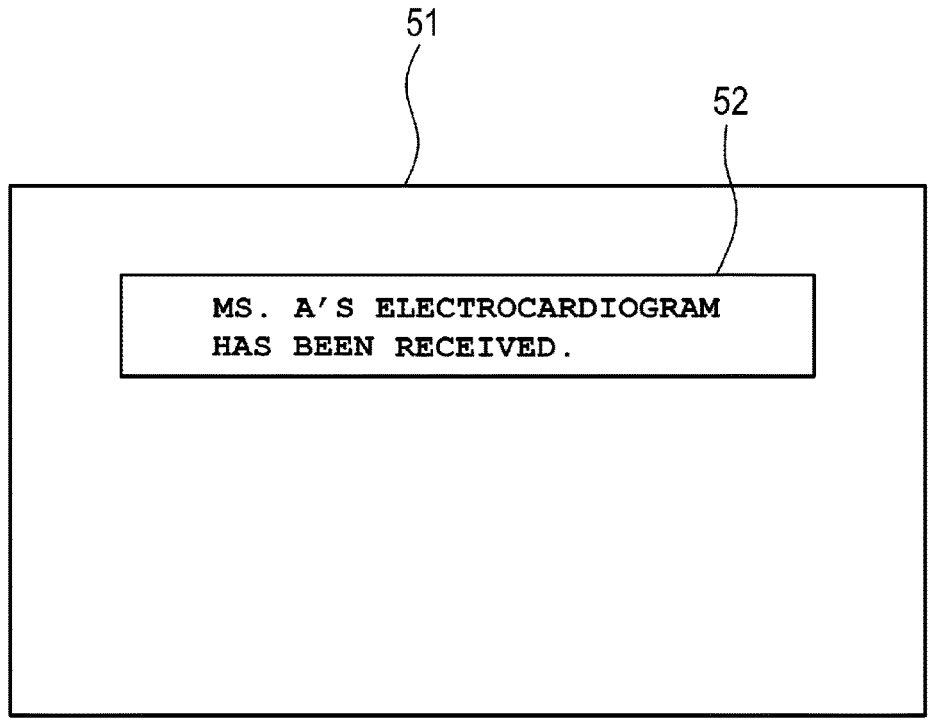
[Fig. 4]
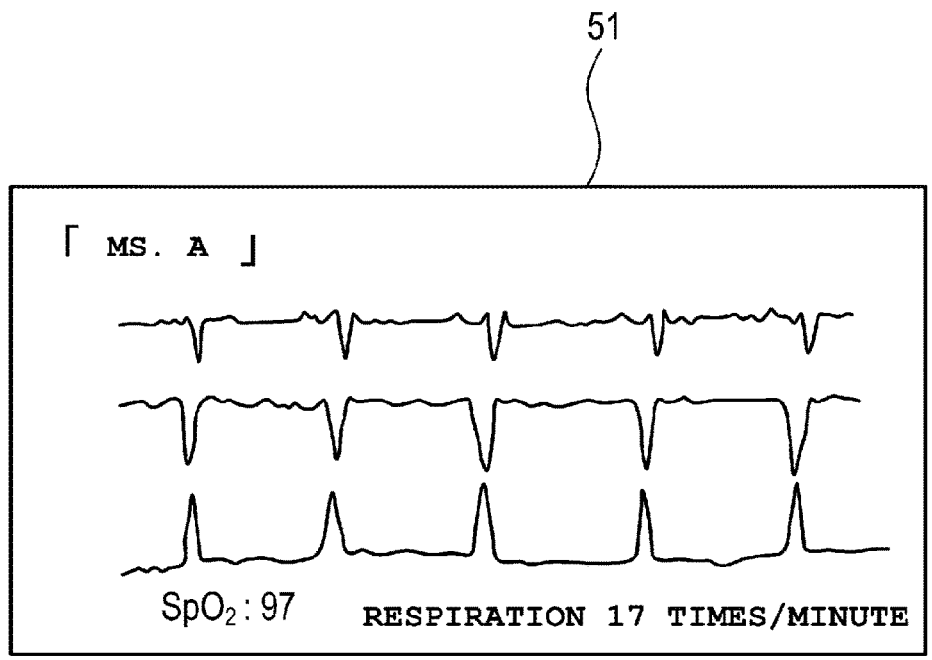

RELAY DEVICE

TECHNICAL FIELD

The present invention relates to a relay device for performing relay of information transmission.

BACKGROUND ART

Assume that a sensor which is attached to a patient is connected to a display device by a cable (wire). In such a configuration, movement of the patent may be restricted by the cable. To solve this problem, for example, there is a system having a configuration in which a sensor can communicate with a display device by wireless (see Patent Literature 1).

CITATION LIST

Patent Literature

PTL 1: U.S. Pat. No. 8,558,933

SUMMARY OF INVENTION

Technical Problem

However, in the system according to Patent Literature 1, when a plurality of patients are at a short distance from the display device, wireless communication between one sensor and the display device may be crossed with wireless communication between another sensor and the display device. Thus, in an anticipated situation, pieces of vital information measured by the sensors cannot be associated with the patients accurately respectively.

Therefore, an object of the invention is to provide a relay device which can support accurate association between vital information measured by a sensor and a patient.

Solution to Problem

In order to achieve the foregoing object, the relay device according to the invention includes: an authentication unit which authenticates a sensor present within a predetermined range; an acquisition unit which can acquire, from the sensor authenticated by the authentication unit, vital information of a patient measured by the sensor; a storage unit in which medical facility identification information associated with a medical facility is stored; and a transmission unit which associates the medical facility identification information with the vital information acquired by the acquisition unit and then transmits the vital information including the medical facility identification information to an external device.

According to the configuration, the relay device is placed in the medical facility (a bed, a private room, or the like) which is, for example, managed in association with the patient on a nurse call system. Thus, when the patient approaches the medical facility and moves into the predetermined range, the vital information including the associated medical facility identification information of the medical facility is transmitted to the external device. The external device can refer to the medical facility identification information and a patient table on the nurse call system so as to associate the received vital information with the patient accurately.

According to the relay device according to the invention, it is possible to support accurate association between the vital information measured by the sensor and the patient.

BRIEF DESCRIPTION OF DRAWINGS

FIG. 1A schematic view showing a use example of relay devices according to an embodiment of the invention.

FIG. 2A block diagram for explaining functions of each of the relay devices.

FIG. 3A view showing an example of a message image displayed on a bedside monitor.

FIG. 4A view showing an example of vital information displayed on the bedside monitor.

DESCRIPTION OF EMBODIMENTS

An embodiment of the invention will be described below by way of example with reference to the drawings. As shown in FIG. 1, relay devices 1A and 1B (which will be hereinafter referred to as relay devices 1 when described generically) according to the embodiment are placed, for example, in beds 2A and 2B (which are an example of medical facilities and which will be hereinafter referred to as beds 2 when described generically) of a hospital room 100. The relay devices 1A and 1B have unique relay device IDs (ID: identification) respectively. The beds 2A and 2B have unique bed IDs respectively. FIG. 1 shows a state in which patients A and B hospitalized in a room of a hospital are lying on the beds 2A and 2B respectively and vital information of the patients A and B are being measured.

Each of the relay devices 1 has a short range wireless communication function. For example, the relay devices 1 are configured to be able to make wireless communicate (e.g. Bluetooth (registered trademark)) with sensors 3a to 3f (which will be hereinafter referred to as sensors 3 when described generically).

The sensors 3 are attached on the patients in order to measure pieces of vital information of the patients. The sensors 3 are wireless sensors each of which has a short range wireless communication function. In the example, the sensors 3a to 3c are attached on the patient A, and the sensors 3d to 3f are attached on the patient B. The sensors 3 have unique sensor IDs respectively. For example, the sensor IDs may be inscribed respectively on the sensors 3 in a visually recognizable form. Incidentally, examples of the measured pieces of vital information include an electrocardiogram, oxygen saturation ($SpO_2$), body temperature, respiration, etc.

In addition, the relay devices 1A and 1B are connected to bedside monitors 5A and 5B (which are an example of external devices and which will be hereinafter referred to as bedside monitors 5 when described generically) communicably through communication cables 4 respectively. Incidentally, the relay devices 1 and the bedside monitors 5 may be connected to each other respectively by wireless communication (e.g. Bluetooth).

Each of the bedside monitors 5 is placed for a corresponding bed 2 which is used by a corresponding hospitalized patient of the hospital room 100. The bedside monitors 5A and 5B have display screens 51A and 51B respectively so that pieces of vital information of the patients received from the relay devices 1A and 1B can be displayed on the display screens 51A and 51B. In addition, the bedside monitors 5 are configured to be able to make communication with a nurse call system 6 placed in a nurse station 200. Each bedside monitor 5 and the nurse call system 6 can be connected to each other, for example, through a wired cable or a wireless LAN (LAN: Local Area Network).

A patient information table in which information about all hospitalized patients has been recorded is saved in the nurse call system 6. For example, pieces of information including a patient ID, a patient's name, a patient's room number, a bed number (bed ID), an attending doctor, an attending nurse, etc. are stored respectively in association with the patients in the patient information table. The nurse call system 6 can transmit the information of the patient information table to the bedside monitors 5 by wireless communication. In addition, the nurse call system 6 has a display screen 61 so that the pieces of vital information of the patients received from the bedside monitors 5 can be displayed on the display screen 61.

In addition, each of the relay devices 1 is configured to be able to make wireless communication (e.g. Bluetooth) with a mobile communication terminal 7 (e.g. a smartphone, a tablet, or the like) held by a medical worker.

For example, the mobile communication terminal 7 registers a sensor ID of a sensor 3 into one of the relay devices 1 by wireless communication. The sensor 3 is scheduled to be used for measurement of vital information. In addition, the mobile communication terminal 7 registers medical facility identification information into the relay device 1 by wireless communication. The medical facility identification information is associated with a medical facility used by a patient whose vital information will be measured by the scheduled sensor 3. For example, a bed, a hospital room, or the like may be included as the medical facility. A bed ID associated with the bed, a hospital room ID associated with the hospital room, or the like can be used as the medical facility identification information. In the example, the bed ID is used as the medical facility identification information because a large room where a plurality of patients are hospitalized is shown as the hospital room 100. On the other hand, the hospital room ID may be used as the medical facility identification information alternatively when the hospital room is a private room. In addition, the mobile communication terminal 7 can communicate with the nurse call system 6 through the aforementioned wireless LAN and receive the information of the patient information table from the nurse call system 6.

ID tags 8A and 8B are attached on parts (such as wrists or ankles) of bodies of the hospitalized patients A and B respectively. Pieces of patient identification information which can identify the patients are stored in the ID tags 8A and 8B respectively. For example, the ID tags 8A and 8B are attached to wristbands. For example, a patient ID, a patient's name, a patient's registration card number, etc. may be included in each of the pieces of patient identification information. The piece of patient identification information may be inscribed to be visually recognizable on the corresponding wristband. Incidentally, here, the term "inscribe" may mean to include a form in which, for example, the wristband has a liquid crystal screen so that the patient identification information such as the patient's name can be displayed on the liquid crystal screen in accordance with a button operation etc.

As shown in FIG. 2, each of the relay devices 1 is provided with an authentication unit 11 which can authenticate sensors 3 present within a predetermined range. The predetermined range means a wirelessly communicable area of the relay device 1. The term "authenticate" means to recognize predetermined sensors 3 selected in advance from the sensors 3 present within the wirelessly communicable area, so as to establish a communicable state with the recognized sensors 3.

The relay device 1 is provided with an acquisition unit 12 which can acquire vital information of a patient measured by the sensors 3 by wireless communication. The acquisition unit 12 acquires the vital information measured by the sensors 3 authenticated by the authentication unit 11.

In addition, the relay device 1 is provided with a storage unit 13 which can store medical facility identification information associated with a medical facility used by the patient, sensor IDs of the sensors 3 measuring the vital information, etc. By wireless communication, the medical facility identification information, the sensor IDs, etc. can be transmitted to the storage unit 13, for example, from the portable communication terminal 7 held by the medical worker.

In addition, the relay device 1 is provided with a transmission unit 14 which can transmit the vital information measured by the sensors 3 to the bedside monitor 5. The transmission unit 14 associates the medical facility identification information stored in the storage unit 13 with the vital information of the patient acquired from the acquisition unit 12, and then transmits the vital information including the medical facility identification information to the bedside monitor 5.

In addition, the relay device 1 is provided with a battery unit 15 which can feed electric power to the respective portions of the relay device 1.

Next, operation of the relay devices 1 will be described with reference to FIGS. 1 to 4. First, as initial setting, a patient information table about patients (e.g. call the patient A and the patient B) whose hospitalization has been determined is generated on the nurse call system 6. In addition, for example, a wristband on which the name (Ms. A) of the patient A has been inscribed and to which the tag ID 8A has been attached may be attached on a wrist of the patient A. Similarly, a wristband on which the name (Ms. B) of the patient B has been inscribed and to which the tag ID 8B has been attached may be attached on a wrist of the patient B. In the hospital room 100, the relay device 1A is placed in the bed 2A where the patient A is hospitalized, and the relay device 1B is placed in the bed 2B where the patient B is hospitalized.

Successively, the medical worker goes to the hospital room 100 where the patient A is hospitalized in order to measure vital information of the patient A. The medical worker registers the bed ID of the bed 2A into the relay device 1A, for example, by use of the smartphone 7, so as to associate the relay device 1A and the bed 2A with each other. For example, the medical worker starts up an "association" application which has been installed in the smartphone 7, and then designates "relay device association". The smartphone 7 on which the relay device association has been designated identifies relay devices present within a wirelessly communicable area, and displays relay device IDs of the identified relay devices on a screen of the smartphone 7. In the case of the example, the relay device ID of the relay device 1A and the relay device ID of the relay device 1B are identified and displayed on the screen of the smartphone 7. From the screen of the smartphone 7, the medical worker selects the relay device ID of the relay device 1A placed in the bed 2A on which the patient A is lying. Thus, the smartphone 7 and the relay device 1A can communicate with each other.

The medical worker designates "medical facility association" in the association application. The smartphone 7 on which the medical facility association has been designated operates in a similar manner to that in the aforementioned case of the relay device association. Consequently, for example, the bed ID of the bed 2A on which the patient A is lying and the bed ID of the bed 2B on which the patient B is lying are identified by the smartphone 7 and displayed on the screen of the smartphone 7. From the screen of the smartphone 7, the medical worker selects the bed ID of the bed 2A on which the patient A is lying. Thus, the bed ID of the bed 2A is transmitted from the smartphone 7 to the relay device 1A. As a result, association between the relay device 1A and the bed 2A is completed. The transmitted bed ID is stored in the storage unit 13 of the relay device 1A. Incidentally, association between the relay device 1 and the bed 2 may be completed in advance in the initial setting.

The medical worker registers the sensor IDs of the sensors 3a to 3c into the relay device 1A to associate the relay device 1A with the sensors 3a to 3c. For example, the medical worker designates "sensor association" in the association application. The smartphone 7 on which the sensor association has been designated operates in a similar manner to that in the aforementioned case of the relay device association. Consequently, for example, the sensor IDs of the sensors 3a to 3c and sensor IDs of the sensors 3d to 3f are identified by the smartphone 7 and displayed on the screen of the smartphone 7. The sensors 3a to 3c are prepared to be used on the patient A on the bed 2A. The sensors 3d to 3f are attached on the patient B on the bed 2B. From the screen of the smartphone 7, the medical worker selects the sensor IDs of the sensors 3a to 3c scheduled to be used on the patient A. Thus, the sensor IDs of the sensors 3a to 3c are transmitted to the relay device 1A from the smartphone 7. As a result, association between the relay device 1A and the sensors 3a to 3c is completed. The transmitted sensor IDs are stored in the storage unit 13 of the relay device 1A. Incidentally, an input interface may be provided in the relay device 1 so that the medical worker can perform the association through the input interface.

Successively, the medical worker attaches the sensors 3a to 3c associated with the relay device 1A, onto the patient A who is lying on the bed 2A. Incidentally, the association of the aforementioned sensors 3a to 3c may be performed after the sensors 3a to 3c are attached on the patient A. The sensors 3a to 3c start detection of vital information of the patient A on which the sensors 3a to 3c are attached, and transmit the measured vital information to the relay device 1A by wireless.

For example, the relay device 1A identifies the sensors 3a to 3f present within the wirelessly communicable area. From the identified sensors 3a to 3f, the authentication unit 11 of the relay device 1A authenticates the sensors 3a to 3c based on the sensor IDs stored in the storage unit 13. The acquisition unit 12 of the relay device 1A acquires the vital information of the patient A transmitted from the authenticated sensors 3a to 3c. The transmission unit 14 of the relay device 1A associates the bed ID of the bed 2A stored in the storage unit 13 with the acquired vital information, and transmits the bed ID-including vital information to which the bed ID has been associated, to the bedside monitor 5A through the communication cable 4. The transmission unit 14 writes the bed ID, for example, into a header area, and then transmits the bed ID-including vital information in which the vital information is written into a data region following the latter part of the header area.

Upon reception of the bed ID-including vital information, the bedside monitor 5A refers to the patient information table held by the nurse call system 6 of the nurse station 200 so as to specify the name ("Ms. A") of the patient A associated with the bed ID. The bedside monitor 5A displays a message indicating "Ms. A's vital information has been received" as a pop-up screen 52, on the display screen 51, for example, as shown in FIG. 3. The medical worker confirms display contents of the pop-up screen 52, and confirms whether Ms. A is the patient herself or not, for example, by the name inscribed on the wristband. Then, the medical worker touches the pop-up screen 52. In the bedside monitor 5A, the pop-up screen 52 is cancelled, and the vital information of the patient A, for example, together with the name ("Ms. A") of the patient A, is displayed on the display screen 51, as shown in FIG. 4.

By an operation on the nurse call system 6, each vital information of the patient A displayed on the aforementioned bedside monitor 5A can be transmitted from the bedside monitor 5A to the nurse call system 6 by wireless, and displayed on the display screen 61 of the nurse call system 6.

In addition, the relay device 1A transmits an alarm signal to the bedside monitor 5A when signals from the sensors 3a to 3c measuring the vital information cannot be received by the relay device 1A, for example, when the sensors 3a to 3c are out of the wirelessly communicable area of the relay device 1A. Upon reception of the alarm signal, for example, the bedside monitor 5A outputs the alarm sound so as to inform of the situation. The bedside monitor 5A may transmit the alarm signal to the nurse call system 6 of the nurse station 200.

Recently, lots of medical institutions have introduced nurse call systems by which patient information is centrally managed. In such a nurse call system, for example, patient identification information which can identify a patient and information about a bed number, a private room number, a medical worker, etc. are associated with each other and managed, for example, by a patient information table. For example, assume that sensors a1 to a3 (not shown) are attached on a patient A, and sensors b1 to b3 (not shown) are attached on a patient B in a background-art medical device which measures patient information by use of wireless sensors. In such a case, the medical device which has received information from the sensors cannot make automatic association for showing that information of the sensor a1 is information of the patient A. In this case, for example, it is considered that device numbers given to the sensors respectively may be associated with the patient information. There is however a possibility that a human error may occur in the association work. In addition, the device numbers of the sensors are often not managed by the patient information table so that association of the nurse call system cannot be used. In addition, for example, it is also considered that the patient identification information may be inputted manually in accordance with each sensor and associated therewith. There is however a possibility that a human error may occur similarly to that in the aforementioned case. In addition, whenever the patient is replaced by another person, work for deleting the associated patient identification information is required to thereby result in an increase in workload.

In light of the fact that each patient spends a lot of time in a hospital room or on a bed of the hospital room, the present inventor has therefore considered an idea of identifying the hospital room itself or the bed itself and associating vital information measured from the patient with a hospital room ID or a bed ID. According to the relay device 1 according to the embodiment, the bed ID of the bed 2A and the sensor IDs of the sensors 3a to 3c scheduled to be used on the patient A are registered in advance into the storage unit 13 of the relay device 1A placed in the bed 2A, for example, through the smartphone 7 when, for example, the patient A is hospitalized on the bed 2A. Therefore, the relay device 1A can authenticate the sensors 3a to 3c registered in the storage unit 13, for example, from the sensors 3a to 3f identified within the wirelessly communicable area, and receive only the vital information transmitted from the sensors 3a to 3c. The relay device 1A can associate the bed ID of the bed 2A stored in the storage unit 13 with the received vital information of the patient A, and transmit the bed ID-including vital information to the bedside monitor 5A. Thus, the bedside monitor 5A can refer to the bed ID of the received bed ID-including vital information and the patient information table on the nurse call system 6 to thereby associate the vital information with the patient A ("Ms. A") accurately. Thus, the bedside monitor 5A can display the vital information associated with the patient A on the display screen 51A etc. Such association can be also performed in a similar manner, when, for example, the hospital room ID is used.

In addition, the relay device 1 is not carried by each patient but placed in each bed 2 used by the patient. Therefore, the degree of freedom for design about the weight or size of the relay device 1 may increase so that a battery can be provided in the relay device 1.

In addition, the vital information of the patient transmitted to the bedside monitor 5 is transmitted not from each sensor 3 but from the relay device 1 placed in the bed 2. Therefore, the relay device 1 and the bedside monitor 5 can be connected to each other by use of the communication cable 4. Accordingly, a signal can be received and transmitted between the relay device 1 and the bedside monitor 5 through the communication cable 4.

In addition, when the sensors 3 authenticated by the relay device 1 are out of the wirelessly communicable area of the relay device 1, an alarm signal is transmitted from the relay device 1 to the bedside monitor 5A. Therefore, the medical worker can quickly know that the patient on which the sensors 3 are attached has moved to another place, for example, from the periphery of the bed 2 where the relay device 1 is placed.

Incidentally, the invention is not limited to the aforementioned embodiment. Any modification, improvement, etc. can be made on the invention desirably and suitably. Besides, the materials, shapes, dimensions, numerical values, forms, numbers, arrangement places etc. of the respective constituent elements in the aforementioned embodiment are not limited but may be set desirably as long as the invention can be achieved.

The present application is based on Japanese Patent Application No. 2016-127895 filed on Jun. 28, 2016, the contents of which are hereby incorporated by reference.

1 (1A, 1B): relay device, 2 (2A, 2B): bed, 3 (3a to 3f): sensor, 4: communication cable, 5 (5A. 5B): bedside monitor, 6: nurse call system, 7: mobile communication terminal, 11: authentication unit, 12: acquisition unit, 13: storage unit, 14: transmission unit, 15: battery unit, 51A, 51B, 61: display screen, 100: hospital room, 200: nurse station

What is claimed is:

1. A relay device comprising:
   a processor configured to:
      authenticate a sensor present within a predetermined range; and
      acquire, from the authenticated sensor, vital information of a patient measured by the sensor;
   a memory configured to store medical facility identification information, the medical facility identification information being information associated with a medical facility; and
   a transmitter configured to associate the medical facility identification information with the vital information and then transmit the vital information including the medical facility identification information to an external device.

2. The relay device according to claim 1, further comprising:
   a battery.

3. The relay device according to claim 1, further comprising:
   a communication cable which is connected to the external device.

4. The relay device according to claim 1, wherein:
   the relay device is configured to transmit an alarm signal to the external device when the sensor moves out of the predetermined range.

5. A relay method comprising:
   authenticating at a relay device, a sensor present within a predetermined range; and
   acquiring at the relay device, from the authenticated sensor, vital information of a patient measured by the sensor;
   storing at the relay device, medical facility identification information, the medical facility identification information being associated with a medical facility; and
   associating at the relay device, the medical facility identification information with the vital information and then transmitting the vital information including the medical facility identification information from the relay device to an external device.

6. The relay method according to claim 5, further comprising:
   transmitting an alarm signal to the external device when the sensor moves out of the predetermined range.

7. The relay device according to claim 1, wherein the medical facility identification information comprises a bed identification or a hospital room identification.

8. The relay method according to claim 5, wherein the medical facility identification information comprises a bed identification or a hospital room identification.

* * * * *